United States Patent
Levy et al.

(10) Patent No.: US 7,482,446 B2
(45) Date of Patent: Jan. 27, 2009

(54) AMIDE-BASED COMPOUNDS, PRODUCTION, RECOVERY, PURIFICATION AND USES THEREOF

(75) Inventors: Alan Levy, Randolph, NJ (US);
Gregory Cleotelis, II, Richmond, VA (US); James Sawyer, Petersburg, VA (US); Nolan Henrich, III, Chesterfield, VA (US); Mohammed Loya, Richmond, VA (US); Matthew Warren, Richmond, VA (US); Gregory Moore, Clemont, FL (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 11/311,604

(22) Filed: Dec. 19, 2005

(65) Prior Publication Data

US 2006/0094873 A1     May 4, 2006

Related U.S. Application Data

(62) Division of application No. 10/251,335, filed on Sep. 21, 2002, now Pat. No. 7,022,844.

(51) Int. Cl.
*C07D 201/04* (2006.01)
*C07D 201/16* (2006.01)

(52) U.S. Cl. ..................................... 540/535; 540/540

(58) Field of Classification Search ................ 540/485, 540/535, 540

See application file for complete search history.

*Primary Examiner*—Bruck Kifle
(74) *Attorney, Agent, or Firm*—Sandra P. Thompson; Buchalter Nemer

(57) ABSTRACT

Methods are disclosed of producing and purifying at least one amide. In accordance with one of the methods disclosed herein, the at least one amide is produced by providing an organic liquid comprising at least one oxime, providing at least one catalyst, adding the at least one catalyst to the organic liquid to form a rearrangement mass, wherein the rearrangement mass comprises at least one amide, at least one impurity, and the at least one catalyst, and heating the rearrangement mass to a temperature of at least about 115° C. for a period of time in order to sulfonate, break down and/or reduce the concentration of some of the at least one impurity in the rearrangement mass.

5 Claims, No Drawings

AMIDE-BASED COMPOUNDS, PRODUCTION, RECOVERY, PURIFICATION AND USES THEREOF

"This application is a divisional of allowed application Ser No. 10/251,335, filed Sep. 21, 2002 now U.S. Pat. No. 7,022, 844, which is incorporated herein by reference in its entirety."

FIELD OF THE INVENTION

The field of the invention relates generally to amide-based compounds and more particularly to ε-caprolactam.

BACKGROUND

In order to control production of plastics, textiles, fibers and adhesive materials, industries involved in their production have quality standards for initial chemical reactants, chemical intermediates and related by-products. These industries are also concerned with streamlining any purification processes and minimizing the amount of by-products and impurities that need to be collected, treated and either recycled or disposed of by the manufacturer. Minimizing the by-products and impurities in the chemical reactants and intermediates can also decrease the number of purification steps and ultimately decrease the cost of production of the final product.

U.S. Pat. No. 3,850,910 (issued to Goettsch on Nov. 26, 1974) shows a typical/conventional process for the production and recovery of pure ε-caprolactam. In Goettsch, the crude caprolactam product is purified through a series of cation and anion exchangers that remove impurities. However, the Goettsch process results in caprolactam yields that may be considered suitable for conventional processes, but are not considered suitable yields when trying to improve the commercial viability of a process or method of producing and/or purifying ε-caprolactam.

US Issued patent application No. 2002/0040137 A1 by Holerich et al. and "Beckmann Rearrangement of Cyclohexanone Oxime over Borate-Pillared LDHs" from *J. Chin. Chem. Soc.*, Vol. 46, No. 5, 1999 describe processes that attempt to purify crude caprolactam. However, these processes utilize technologies that may not translate well into a commercial purification process, such as fluidized beds and borate-pillared LDHs, or may be considered too costly and/or bulky to use or incorporate into a commercial production/purification process.

U.S. Pat. No. 4,017,482 (issued to Gath on Apr. 12, 1977) describes a process of combining crude caprolactam obtained from a Beckmann rearrangement of cyclohexanone oxime in oleum with the gas-phase rearrangement of cyclohexanone oxime in the presence of catalysts. This process of simultaneously purifying two different sources of crude caprolactam requires several additional and possibly unnecessary processing steps that would hinder an efficient commercial amide production method and/or process. Moreover, this process is not practiced commercially.

U.S. Pat. No. 4,804,754 (issued to DeDecker et al. on Feb. 14, 1989) discloses a process of purifying a single stream of crude caprolactam by after treating the reaction mixture in a relatively low temperature delay zone, which can be an elongated structure or large tube, for a specified time period of 10 to 600 minutes. However, the temperature contemplated by DeDecker does not exceed the maximum temperatures specified for a successful Beckmann rearrangement, which can lead to lengthy processing times and delay times while the crude caprolactam is in the aftertreatment stage.

Based on industry standards, cost concerns, environmental concerns and quality assurance standards, methods should be utilized that a) remove or reduce the amount of significant or influential impurities in the chemical reactant or intermediate; b) facilitate removal or reduction of significant or influential impurities in the chemical reactant or intermediate; and c) streamline the process of further production incorporating the chemical reactant or intermediate.

As described herein, in order to produce at least one of the amide compounds described herein, including lactams and ε-caprolactam, a method of production has been developed that not only produces at least one amide compound, but also reduces or substantially eliminates certain impurities and thus improves the quality of the amide compound and can improve any of the products produced using the amide compound. The method of producing at least one amide comprises: a) providing an organic liquid comprising at least one oxime (subsequently referred to as liquid oxime); b) providing at least one catalyst; c) adding the at least one catalyst to the liquid to form a rearrangement mass, wherein the rearrangement mass comprises at least one amide, at least one impurity, and the at least one catalyst; and d) heating the rearrangement mass in order to sulfonate, break down and/or significantly reduce at least some of the at least one impurity in the rearrangement mass.

Upon and after heating, the rearrangement mass will comprise at least one amide, at least one catalyst and at least one broken down or sulfonated impurity and/or an impurity that has been reduced in concentration. At this point, the at least one amide should be removed from the remaining constituents of the post-heating step rearrangement mass by using a purification method. A contemplated method of purifying the at least one amide comprises: a) adding water, a base and solvent to the rearrangement mass to form a neutralized solution; b) separating the neutralized solution into an aqueous phase and an organic phase; c) distilling the organic phase to produce a solvent distillate and an impure amide; d) performing a crystallization purification step on the impure amide; and e) distilling and drying the crystallization amide product to produce a final purified amide product.

SUMMARY OF THE INVENTION

The subject matter herein is directed to a method of producing at least one amide. In accordance with method of the present invention, the at least one amide is produced by providing an organic liquid comprising at least one oxime, providing at least one catalyst, adding the at least one catalyst to the organic liquid to form a rearrangement mass, wherein the rearrangement mass comprises at least one amide, at least one impurity, and the at least one catalyst, and heating the rearrangement mass to a temperature of at least about 115° C. for a period of time in order to sulfonate some of the at least one impurity in the rearrangement mass.

The subject matter herein is further directed to a method of producing at least one amide. In accordance with method of the present invention, the at least one amide is produced by providing an organic phase comprising at least one oxime, providing at least one catalyst, adding the at least one catalyst to the organic phase to form a rearrangement mass, wherein the rearrangement mass comprises at least one amide, at least one impurity, and the at least one catalyst, and heating the rearrangement mass to a temperature above about 115° C. for a period of time in order to break down some of the at least one impurity in the rearrangement mass.

DETAILED DESCRIPTION

Chemicals that are used as intermediates in another process or as building blocks and/or starting materials in a manufacturing process generally should be produced and subsequently purified, if necessary, to meet or exceed the industry specifications or quality standards for that particular chemical, intermediate, material or compound. The production and purification processes may comprise a) removing the impurities found in the rearrangement mass and/or organic phase altogether and/or b) converting some or all of the impurities to other insignificant compounds. As used herein, the term "insignificant" is used to express that quantity relative to the main component being measured with respect to industry specifications and quality standard measurements.

Amides are an important group of nitrogenous compounds that are used as intermediates and/or building blocks in the production of textiles, plastics and adhesives. Amides are generally represented by the following formula:

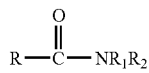

wherein R is an alkyl group, an aryl group, a cyclic alkyl group, an alkenyl group, an arylalkylene group, or any other appropriate group that can be utilized to be a part of an amide compound. $R_1$ and $R_2$ may independently be hydrogen or any of the substituent groups previously mentioned.

The term "alkyl" is used herein to mean a branched or a straight-chain saturated hydrocarbon group or substituent of 1 to 24 carbon atoms, such as methyl, ethyl, n-propyl, isopropyl, n-butyl, isobutyl, t-butyl, octyl, decyl, tetradecyl, hexadecyl, eicosyl, tetracosyl and the like. In some embodiments, contemplated alkyl groups contain 1 to 12 carbon atoms. The term "cyclic alkyl" means an alkyl compound whose structure is characterized by one or more closed rings. The cyclic alkyl may be mono-, bi-, tri- or polycyclic depending on the number of rings present in the compound.

The term "aryl" is used herein to mean a monocyclic aromatic species of 5 to 7 carbon atoms or a compound that is built with monocyclic aromatic species of 5 to 7 carbon atoms and is typically phenyl, naphthalyl, phenanthryl, anthracyl etc. Optionally, these groups are substituted with one to four, more preferably one to two alkyl, alkoxy, hydroxy, and/or nitro substituents.

The term "alkenyl" is used herein to mean a branched or a straight-chain hydrocarbon chain containing from 2 to 24 carbon atoms and at least one double bond. Preferred alkenyl groups herein contain 1 to 12 carbon atoms.

The term "alkoxy" is used herein to mean an alkyl group bound through a single, terminal ether linkage; that is, an alkoxy group may be defined as —OR wherein R is an alkyl group, as defined above.

The term "arylalkylene" is used herein to mean moieties containing both alkylene and monocyclic aryl species, typically containing less than about 12 carbon atoms in the alkylene portion, and wherein the aryl substituent is bonded to the structure of interest through an alkylene linking group. Exemplary arylalkylene groups have the structure —$(CH_2)_j$—Ar wherein "j" is an integer in the range of 1 to 6 and wherein "Ar" is an aryl species.

Amides can also be straight-chain, branched, substituted and cyclic. Cyclic amides are often referred to as "lactams", which are produced from amino acids by the removal of one molecule of water. Exemplary amides include acetamides, acrylamides, anilides, benzamides, benzoylarginine-2-naphthylamide, formamides, lactams, salicylamides, sulfonamides and thioamides. An example of a cyclic amide is a lactam, such as caprolactam or ε-caprolactam.

ε-Caprolactam, also known as aminocaproic lactam and 2-oxohexamethyleneimine, is a compound that is produced in flake and molten forms and is used primarily in the manufacture of Nylon-6 products such as synthetic fibers, plastics, bristles, films, coatings, synthetic leathers, plasticizers and paint vehicles. Caprolactam can also be used as a cross-linking agent for polyurethanes and in the synthesis of the amino acid lysine.

Amides, such as caprolactam, are generally produced by reacting a ketone with hydroxylamine to make an oxime, and then using an acid catalyzed rearrangement of the oxime(s), conventionally called the Beckmann rearrangement, to form the amide. Two examples of the Beckmann rearrangement process are shown below:

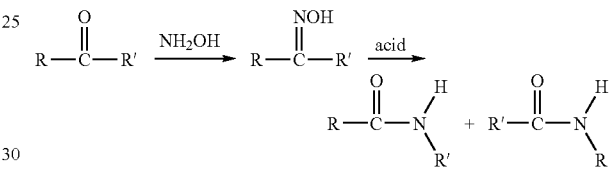

EXAMPLE 1

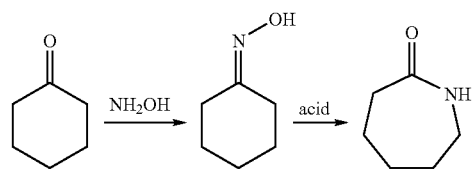

EXAMPLE 2

When producing merchant quality caprolactam, certain properties of the caprolactam should be quantified, such as transmittance, color and permanganate number. Transmittance for caprolactam is measured as UV transmittance at 290 nm. Color is measured by using colorimetric analysis and is usually expressed in APHA standard color units. The permanganate absorption number or permanganate number is related to the number of oxidizable impurities in caprolactam, as determined in a buffered neutral aqueous medium by treatment with potassium permanganate solution.

In order to produce at least one of the amide compounds described herein, including caprolactam, a method of production has been developed that not only produces at least one amide compound, but also significantly reduces certain impurities and thus improves the quality of the final amide compound and can improve the quality of any product produced using the amide compound. The method of producing at least one amide comprises: a) providing an organic liquid comprising at least one oxime (referred to herein as either "liquid oxime" or "organic liquid"); b) providing at least one catalyst;

c) adding the at least one catalyst to the liquid oxime to form a rearrangement mass, wherein the rearrangement mass comprises at least one amide, at least one impurity, and the at least one catalyst; and d) heating the rearrangement mass in order to sulfonate, break down, or significantly reduce the concentration of the at least one impurity in the rearrangement mass.

Initially, an organic liquid is provided, produced or formed that comprises at least one oxime. As used herein, the term "oxime" means that product resulting from the reaction of a ketone with hydroxylamine. One general reaction that forms an oxime is shown below:

EXAMPLE 3

In some embodiments, the oxime is a keto-oxime, which is otherwise known as a ketoxime or ketone oxime. In other embodiments, the oxime is a cyclic keto-oxime. And in yet other embodiments, the oxime is cyclohexanone oxime. The liquid oxime and/or its components can be provided by any suitable method known in the art, such as: 1) preparation of the entire liquid oxime in a the laboratory setting or in a commercial setting where the rest of the amide production and purification will take place; 2) preparation of part of the liquid oxime and/or its components in the laboratory setting or commercial setting where the rest of the amide production and purification will take place; or 3) acquiring some or all of the liquid oxime and/or its components from outside of the laboratory setting or setting where the rest of the amide production and purification will take place. The components of the liquid oxime may be obtained from a university, a chemical supplier or another independent supplier.

At least one catalyst is provided that will be added or introduced to the liquid oxime. As used herein, the term "catalyst" means any substance that affects the rate of the chemical reaction without itself being consumed or undergoing a chemical change. Catalysts may be inorganic, organic, or a complex of organic groups and metal halides. Catalysts may also be liquids, solids, gases or a combination thereof.

In some embodiments, the catalyst is an acid catalyst or strong acid, such as oleum, a compound that comprises sulfuric acid and sulfur trioxide. In some embodiments, the oleum catalyst comprises a sulfur trioxide content of about 15% to less than about 40% using a weight percent basis. In other embodiments, the catalyst comprises a sulfur trioxide content of about 20% to about 30% using a weight percent basis. And in yet other embodiments, the catalyst comprises a sulfur trioxide content of about 25% using a weight percent basis. In some contemplated embodiments, the weight percentage of sulfur trioxide in the rearrangement mass is from about 1% to about 10%. In other contemplated embodiments, the weight percentage of sulfur trioxide in the rearrangement mass is from about 1% to about 5%. And in yet other contemplated embodiments, the weight percentage of sulfur trioxide in the rearrangement mass is from about 2% to about 4%.

In contemplated embodiments, the catalyst is oleum, and the weight ratio of oleum to oxime is generally 2:1 to 0.8:1. Based on these ratios, in a contemplated embodiment, there are about 1 to 2 parts of catalyst to every one part of ketoxime, using a weight ratio basis, such as the case with ketoxime and oleum. In other embodiments, the weight ratio of catalyst to oxime is from about 1.6:1 to about 1:1, such as the case with one mixture of oleum and cyclic ketoxime. In yet other embodiments, the weight ratio of catalyst to oxime is from about 1.25:1 to about 1.05:1, such as the case with another mixture of oleum and cyclic ketoxime.

At this point it should be understood that, unless otherwise indicated, all numbers expressing quantities of ingredients, constituents, reaction conditions and so forth used in the specification and claims are to be understood as being modified in all instances by the term "about". Accordingly, unless indicated to the contrary, the numerical parameters set forth in the specification and attached claims are approximations that may vary depending upon the desired properties sought to be obtained by the subject matter presented herein. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the subject matter presented herein are approximations, the numerical values set forth in the specific examples are reported as precisely as possible. Any numerical value, however, inherently contain certain errors necessarily resulting from the standard deviation found in their respective testing measurements.

It is understood that the Beckmann rearrangement reaction can be conducted at a temperature less than about 110° C. In some instances, the Beckmann rearrangement reaction is conducted at temperatures of 75° C. to 110° C., and preferably conducted at temperatures of 75° C. to 90° C.

The liquid oxime and the at least one catalyst are added or introduced to one another such that there is a chemical reaction that forms a rearrangement mass. As used herein, the phrase "rearrangement mass" means the mixture of at least one amide, at least one impurity and the at least one catalyst. Also, as used herein, the term "impurity" means any component of the rearrangement mass that is not the at least one amide or the at least one catalyst. The at least one impurity can be present in the rearrangement mass in any concentration, depending on the chemical reaction that takes place upon addition or introduction of the catalyst to the organic phase solution. In some embodiments, the at least one impurity comprises a pyrazine precursor compound, such as an octahydrophenazine (OHP) compound precursor. OHP itself is a major cause of unacceptable UV transmittance in the final amide products. In other embodiments, the at least one impurity may comprise partially reacted products, unwanted isomers, and other similar compounds and compositions.

The rearrangement mass is then heated in order to sulfonate, break down or significantly reduce some or all of the previously described impurities in the rearrangement mass. The rearrangement mass may be heated by any suitable heating method and/or apparatus. In some embodiments, the rearrangement mass may be heated by using heat transfer equipment, heat transfer fluid, heat exchangers, steam, water, oil, air, another mass capable of conducting or transferring heat, gas fired burners, electric heaters, hot oil jackets, process fluids and/or any combination thereof. As far as a suitable or appropriate temperature for the rearrangement mass during the heating step, in contemplated embodiments, the rearrangement mass will be heated to and maintained at temperatures at or above about 115° C. In other embodiments, the rearrangement mass will be heated to and maintained at a temperature at or above about 115° C. to about 140° C. In yet other embodiments, the rearrangement mass will be heated to and maintained at a temperature at or above about 115° C. to about 130° C. or at or above about 120° C. to about 125° C. In any event, it should be understood that the step of heating the rearrangement mass in order to sulfonate, break down or significantly reduce some or all of the at least one impurity in the rearrangement mass is contemplated to be a separate heating step from the heating that takes place during the Beckmann rearrangement reaction. It should also be understood that the step of heating the rearrangement mass in order to sulfonate, break down or significantly reduce some or all of the at least one impurity in the rearrangement mass is contemplated to take place at higher temperatures than the temperatures used for conducting a conventional Beckmann rearrangement reaction.

The step of heating the rearrangement mass in order to sulfonate, break down or significantly reduce some or all of the at least one impurity in the rearrangement mass should also take into account the time the mass is maintained at a particular temperature or a particular temperature range, as well as taking into account the particular temperature or temperature range. It should be understood that the time of heating is directly related to the heating temperature, with the time of heating decreasing as the heating temperature increases. In some embodiments, the time of heating will range from about 1 minute to about 30 minutes for temperatures ranging from about 115° C. to about 140° C. In other embodiments, the time of heating will range from about 4 minutes to about 30 minutes for temperatures ranging from about 115° C. to about 125° C. In yet other embodiments, the time of heating will range from about 4 minutes to about 16 minutes for temperatures ranging from about 120° C. to about 125° C.

As previously described, the at least one impurity may be sulfonated, broken down, or significantly reduced by heating the rearrangement mass. As used herein, the term "sulfonate" means introducing of a "sulfo" group into an organic compound, whereby the group bonds to a carbon or nitrogen atom in the compound. A "sulfo" group may comprise $SO_2$, $SO_3$, $HSO_3$ and the like. Also, as used herein, the phrase "break down" or "breaking down" or "broken down" are intended to be used interchangeably and mean that the compound or molecule is split apart into a combination of smaller molecules. Also, it should be kept in mind that whether the at least one impurity is sulfonated, broken down or significantly reduced, the resulting compound(s) become additional impurities that can be removed during a subsequent purification process.

The heating process generally produces impurities that are generally easier to remove in full or in part during the purification process, as opposed to those impurities that exist in the rearrangement mass before the heating step. In some embodiments, one or more of the impurities, individually or collectively, are reduced significantly with respect to generally accepted levels of impurities in these types of reactions. In other embodiments, the at least one impurity in the rearrangement mass is reduced to less than about 50 ppm. In yet other embodiments, the at least one impurity is a precursor to OHP, and it is sulfonated, and thus reduced in concentration in the rearrangement mass to less than 50 ppm.

As mentioned, upon and after heating, the rearrangement mass will comprise at least one amide, at least one catalyst and at least one impurity that has been broken down, sulfonated and/or otherwise significantly reduced in concentration with respect to the remaining constituents in the mass and also with respect to generally accepted levels of impurities in these types of reactions. At this point, the at least one amide should be removed from the remaining constituents of the post-heating step rearrangement mass by using a purification method. A contemplated method of purifying the at least one amide comprises: a) adding water, a base and solvent to the rearrangement mass to form a neutralized solution; b) separating the neutralized solution into an aqueous phase and an organic phase; c) distilling the organic phase to produce a solvent distillate and an impure amide; d) performing a crystallization purification step(s) on the impure amide; and e) distilling and drying the crystallization amide product to produce a final purified amide product. Additional and optional purification steps may be included in the basic method in order to further purify the at least one amide.

The amide purification method begins by adding a mixture of water, a base and an organic solvent to the rearrangement mass. As used herein, the term "base" means any compound that can be considered a Lowry-Bronsted base, including any molecular or ionic substance that can combine with a proton (hydrogen ion) to form a new compound. Examples of contemplated bases comprise hydroxyl ion, metal oxides, compounds of oxygen, nitrogen and sulfur with non-bonded electron-pairs, such as ammonia.

Contemplated solvents include any suitable pure or mixture of organic molecules that are volatilized at a desired temperature and/or easily formed into an organic phase. The solvent may also comprise any suitable pure or mixture of polar and non-polar compounds. In some embodiments, the solvent comprises benzene, trichloroethylene, toluene, ethers, cyclohexanone, butryolactone, methylethylketone, and anisole. As used herein, the term "pure" means is composed of a single molecule or compound. For example, pure water is composed solely of $H_2O$. As used herein, the term "mixture" means that component that is not pure, including salt water. As used herein, the term "polar" means that characteristic of a molecule or compound that creates an unequal charge, partial charge or spontaneous charge distribution at one point of or along the molecule or compound. As used herein, the term "non-polar" means that characteristic of a molecule or compound that creates an equal charge, partial charge or spontaneous charge distribution at one point of or along the molecule or compound. Particularly preferred solvents include, but are not limited to, pentane, hexane, heptane, cyclohexane, benzene, toluene, xylene, halogenated solvents such as carbon tetrachloride, and mixtures thereof.

The addition of base, water and solvent to the rearrangement mass causes the constituents of the rearrangement mass to separate out into a dual phase liquid comprising an aqueous phase and an organic phase. In contemplated embodiments, the aqueous phase comprises the water and an acid salt, such as aqueous ammonium sulfate, after separation. The organic phase comprises the organic solvent, such as toluene, the at least one amide, and some or all of the at least one impurity.

The aqueous phase and organic phase are manually separated from one another by using conventional industrial processes such as gravity decanters. The separated aqueous phase at this point can be processed, such that the components of the aqueous phase are separated, purified or otherwise processed in order to be recycled, sold, or disposed of properly and according to industry standards. The ammonium sulfate produced by the process in one of the contemplated embodiments can be further processed and sold as a fertilizer.

The organic phase is distilled by any suitable distillation process, such as vacuum distillation, to form a solvent distillate and an impure amide product. The solvent distillate can be recycled at this point, but it should be understood that the solvent distillate comprises little to no amide compounds. The impure amide product may be treated such that the water content of the impure amide is reduced, such as by vacuum distillation. Then, the at least one amide in the impure amide is purified by a crystallization process(es), distilled and dried to produce a high quality purified amide product. The impure amide or the purified amide product can be further distilled, crystallized and processed in order to remove any residual impurities and to produce a higher quality amide product.

EXAMPLES

Testing/Analytical Methods

The following testing and analytical methods are shown and described in detail below and are referred to by QALAC Number in Tables 1 and 2:

QALAC-0001: Determination of APHA Color of Finished Product Lactam or Caprolactam.

This analytical method describes the process for the determination of APHA color of the finish product caprolactam and/or lactam. Standard eye and hand protection is required.

Glassware associated with standard analytical analysis
Dual beam spectrophotometer(s), Shimadzu UV-1601 or equivalent
10 cm Pyrex cells
Hot water bath
150 mL plastic beakers or equivalent
Thermometer
Cool water bath
Note: The glassware is to be clean, unbroken, and of adequate size and volume capacity to perform this procedure. Adhering to these conditions, and dependent upon availability, technicians are empowered to select and use glassware for the completion of this procedure.

Materials:
Filtered, distilled water
Warm tap water
Purity of water: references to water shall be understood to mean reagent water conforming to the specifications for reagent water. (ASTM Designation D1193).

Amide or caprolactam should be at a temperature of 30° C.+/−1° C. prior to analysis. Allow the sample to warm or cool as needed. Samples may be liquefied in a hot water bath, as necessary. Samples need to be fully molten before use.

Prior to the first sample analysis, typically at the beginning of each 8 hour shift, empty the reference and sample cell and clean each with cell cleaning solution. Rinse the cells with distilled water.

Fill the clean Pyrex cells with filtered, distilled water. Inspect the cells for cleanliness and clean as needed. Inspect the cell compartment windows for cleanliness and clean as needed. Place the sample cell in the sample beam (front position) and the reference cell in the reference beam (rear position) of the cell compartment and close the compartment cover.

Zero the spectrophotometer, observing the following conditions:
Wavelength (390 nm)
Operating Mode (Concentration)
Reference (Filtered, distilled water)
Concentration Multiplier (As posted near instrument)

Transfer 50 mL of filtered, distilled water into the appropriate 150 mL beaker (or equivalent). Transfer 50 g+/−0.05 g of molten or flake sample into the same beaker. Using a thermometer, gently agitate the sample/water mixture until mixed thoroughly and monitor the temperature. Note: a cool water bath may be used to aid cooling. When the sample/water mixture reaches 30° C.+/−1° C., rinse the appropriate cell with the solution and discard the rinsing solution into the appropriate waste container. Refill the sample cell with the sample solution. Cap the cell and invert as necessary to eliminate the concentration gradient lines and/or air bubble in the cell. Inspect the cell for cleanliness, concentration lines and air bubbles before proceeding. Insert the cell into the sample beam (front position in the cell compartment), close the compartment cover, and allow the digital readout to stabilize before printing or recording the result.

The APHA color number is read directly from the instrument readout. When analyzing multiple samples, rinse the cell between readings using the next sample to be analyzed. When all analyses are complete, thoroughly rinse the sample cell with warm water followed by distilled water. Refill the sample cell with filtered, distilled water. Insert the sample cell, as described above to ensure baseline stability. If the instrument fails to re-zero repeat the steps outlined above, as necessary. Re-analyze all samples as per the previous steps.

Upon completion of the color analysis, rinse the sample cell with warm water and then with distilled water. Wipe the outside of the cell dry and store it in the appropriate storage container.

Reporting of APHA color numbers:
For control purposes, finished product results are reported to the nearest 0.1 APHA color unit in the range from 1-10 APHA. Results of less than 1.0 APHA color units are reported as <1.0 APHA units. Results of greater than 10 APHA color units are reported to the nearest 1 APHA color unit.

As determined by a single analyst, the standard deviation is 0.06 APHA units at the 4.3 APHA level for 10 degrees of freedom.

QALAC-0002: Determination of Permanganate Index of Refined and Finished Product Lactam or Caprolactam This analytical procedure describes the method for the determination of the permanganate index of refined and finished product lactam and/or caprolactam. Standard eye and hand protection is required.

Special Tools/Equipment/Materials:
Glassware associated with standard analytical analysis.
Dual beam spectrophotometer, Shimadzu UV-1601 or equivalent.
5 cm Pyrex cells
Timer, with seconds capability
Plastic volumetric flasks, 100 mL, with caps, or equivalent.
Constant temperature bath, capable of maintaining 25° C.+/−0.5° C.
Glassware used is to be clean, unbroken and of adequate size and volume capacity to perform this procedure. Adhering to these conditions, and dependent upon availability, technicians are empowered to select and use glassware for the completion of this procedure.

Materials:
Distilled water, filtered.
0.01N Potassium permanganate ($KMnO_4$)
0.01N Sodium hydroxide (NaOH)— for pH adjustment
0.01N Sulfuric acid ($H_2SO_4$)— for pH adjustment Procedure: Preparation:
The water used in this procedure must adhere to the following conditions:
The water must be filtered and distilled. The pH must be 6.2 to 6.5. If this condition is not met, adjust the pH with 0.01N $H_2SO_4$ (to lower the pH) or 0.01N NaOH (to raise the pH). The filtered, distilled water used in this procedure is acclimated to room temperature. This procedure is typically accomplished with two 20 liter bottles, one being in service while the other is being acclimated. The water and potassium permanganate quality are checked with a blank solution. This blank solution, analyzed under the same conditions as a sample, ensures that the components are of an appropriate quality to achieve a 0.02 absorbance or less as reported earlier. If the absorbance is greater than 0.02, inspect and/or replace the components, then reanalyze the blank.

Prior to the first sample analysis, typically at the beginning of each 8 hour shift, empty the reference cell (if filled) and refill with fresh filtered distilled water. Inspect the cell for cleanliness, clean as needed, and wipe dry. Insert the reference cell into the reference beam (rear position) in the cell compartment.

Note: when using a single beam spectrophotometer, ignore the reference cell and reference beam (rear position) notations.

Fill a clean 5 cm Pyrex cell (sample cell) with filtered, distilled water from the same source as the reference cell. Inspect the cell compartment windows for cleanliness and clean as needed. Place the sample cell in the sample beam (front position) of the cell compartment and close the compartment lid. Zero the spectrophotometer, observing the following conditions:

Wavelength: 420 nm
Operating Mode: Absorbance
Reference: Distilled water, filtered Before the analysis of any samples or blanks, determine the absorbance of the 0.01N potassium permanganate using the 5 cm sample cell and the conditions listed above. If the absorbance of the 0.01N potassium permanganate exceeds 0.600 absorption units, it is not to be used. Fresh 0.01N potassium permanganate is obtained and analyzed. The 0.01N potassium permanganate in service is to be kept in a dark colored bottle and stored in the provided closable storage container when not in use.

Transfer approximately 50-80 mL or filtered, distilled water into a clean 100 mL volumetric flask(s). Transfer 3.0 g, weighed to the nearest 0.01 g, of well mixed molten or flake amide or caprolactam into the volumetric flask (s) and cap. Shipments and finished product storage tank amide and/or caprolactam samples are weighted to the nearest 0.01 g. Other refined amide and/or caprolactam samples need only be weighed to the nearest 0.1 g. One volumetric flask, to be used as a blank, will contain only filtered, distilled water.

Invert and shake the volumetric flask(s) several times to thoroughly mix the solution. Dilute the volumetric flask(s) to the mark with filtered, distilled water. Place the volumetric flask(s) into a constant temperature bath with a maintained temperature of 25° C.+/−0.5° C. for a minimum of 15 minutes.

Sample Analysis:

Remove the volumetric flask(s) from the constant temperature bath, as outlined above. Transfer 2.0 mL of 0.01N potassium permanganate into the volumetric flask(s) and immediately start the timer. When multiple samples are to be analyzed, transfer 2 mL of 0.01N potassium permanganate into each volumetric flask in turn, so that the interval will be comfortable when the absorbance is being determined.

Invert and shake the volumetric flask(s) several times to thoroughly mix the solution and return it into the constant temperature bath. At approximately 9 minutes, remove the first volumetric flask to be analyzed from the constant temperature bath and rinse the sample cell with the solution. Refill the sample cell with the solution.

Cap the cell and invert as necessary to eliminate concentration gradient lines and/or air bubbles in the cell. Inspect the cell for cleanliness, concentration lines and air bubbles. Insert the cell into the sample beam (front position in the cell compartment), close the compartment cover. At 10 minutes, either print or record the absorbance of the solution. Note: If the absorbance of the blank solution exceeds 0.02, analyze another blank solution and all samples that were analyzed in this blank. When analyzing multiple samples, maintain the same timed interval as initiated in an earlier step, and rinse the cell between readings using the next sample to be analyzed.

When all analyses are complete, thoroughly rinse the sample cell with warm water followed by filtered, distilled water. Refill the sample cell with filtered, distilled water. Insert the sample cell as described earlier to ensure baseline stability. If the instrument fails to re-zero, repeat earlier steps as necessary. Re-analyze all samples.

Upon completion of the analysis, rinse the sample cell with warm water and then with distilled water. Wipe the outside of the cell dry and store it in the appropriate storage container.

Calculations:

$$\text{Permanganate Index: } (A-B) \times 10^2 / W$$

Where
A=Absorbance of the sample
B=Absorbance of the blank
$10^2$=Conversion to percent
W=Weight of amide or caprolactam, g Report results to the nearest 0.1 PN unit with results of less than 0.1 being reported as less than 0.1. As determined by a single analyst, the standard deviation is 0.12 at the 2.6 PN for 10 degrees of freedom.

QALAC-0005: Determination of Water in Refined and Finished Product Lactam or Caprolactam (Aquameter Titration)

This analytical procedure describes the method for the determination of the water content of refined and finished product lactam and/or caprolactam. Standard hand and eye protection is required.

Special Tools/Equipment/Material:
Metrohm 701 KF Titrino or equivalent.
Glassware associated with standard analytical analysis.
Hot plate
Flask tongs, or equivalent
Black neoprene gloves
20 cc B-D syringe with 4 in. pipetting needle or equivalent
Drying oven
Glassware used is to be clean, unbroken and of adequate size and volume capacity to perform this procedure. Adhering to these conditions, and dependent upon availability, technicians are empowered to select and use glassware for the completion of this procedure.

Materials:
Aqua Star Comp-5® or Hydranal Comp-5®, Pyridine free Karl Fischer Reagent, or equivalent.
Pre-dried Methanol, technical grade
Note: Purity of reagents—reagent grade chemicals will be used in all solution preparations. Unless otherwise indicated, it is intended that all reagents will conform to the specifications of the committee on analytical reagents of the American Chemical Society, where such specifications are available.

Procedure:

Amide and/or caprolactam solutions must be molten prior to analysis. Caution: the caprolactam for water analysis must be liquefied on a hot plate. Extreme care must be taken when heating these samples. The bottle cap must be loosened before heating to prevent pressure build up. The hot sample bottle(s) should be handled with tongs or with black gloves.

Inspect the titration beaker for cleanliness and methanol volume. Ensure that the Aquameter probe tip is clean and fully immersed in the methanol.

Note: several different models of Aquameters may be in service at any given time. The settings and operational instructions will be covered through training.

Refill the Aquameter buret with Karl Fischer Reagent (if needed). Press the Aquameter start button to preneutralize the methanol. Preneutralization is to be performed at least once immediately prior to sample analysis. Rinse the 20 cc syringe several times with the sample to be analyzed. Note: the syringe used to inject the sample into the Aquameter must be kept warm to prevent freezing.

Immediately after the neutralization end point is reached, inject 20 cc of sample into the titration beaker, taking care not to leave the titration beaker open to the atmosphere for an extended period of time. If the sample is known to have a high (>0.2%) water content, adjust the sample volume (and calculation) accordingly.

Press the Aquameter start button to start the titration. When the titration is completed, record the amount of titrant used. Clean the Aquameter titration beaker after each analysis. Refill the titration beaker with fresh pre-dried methanol and preneutralize with Karl Fischer reagent. The Aquameter may be left in this condition until its next use.

At the completion of the sample analysis, clean the syringe with hot water, followed by methanol rinses. Place the syringe in the drying oven to heat and dry the syringe.

Calculations:
Calculate the concentration of water as follows:

$$\% \text{ Water} = (T \times F \times 100)/V$$

where:
T=titrant volume (mL)
F=standardization factor of Karl Fischer reagent (gm water/mL titrant)
100=100%
V=sample volume (cc)
Note: the density of caprolactam is assumed to be 1.00 μm/mL, therefore 1 mL=1 gm=1 cc Report results to the nearest 0.01%. Results of less than 0.01% are to be reported as <0.01%. As determined by a single analyst, the standard deviation is 0.004% at the 0.03% water level for 10 degrees of freedom.

QALAC-0006: Determination of Free Acidity and Free Alkalinity in Refined and Finished Product Lactam or Caprolactam This analytical procedure describes the method for the determination of Free Acidity and Free Alkalinity of refined and finished product lactam and/or caprolactam. Standard hand and eye protection is required.

Special Tools/Equipment/Materials:
Glassware associated with standard analytical analysis
Microburette, marked in increments of 0.01 mL
Analytical balance, capable of weighing +/−0.01 g
20 cc B-D syringe with tip, or equivalent
Hot water bath
Glassware used is to be clean, unbroken, and of adequate size and volume capacity to perform this procedure. Adhering to these conditions, and dependent upon availability, technicians are empowered to select and use glassware for the completion of this procedure.

Materials:
Demineralized, deionized water
0.02N sodium hydroxide solution
0.02N hydrochloric acid solution
Tashiro's Indicator Solution
Purity of reagents: Reagent grade chemicals will be used in all solution preparations. Unless otherwise indicated, it is intended that all reagents will conform to the specifications of the Committee on Analytical Reagents of the American Chemical Society, where such specifications are available.
Purity of water—References to water shall be understood to mean reagent water conforming to the specifications for reagent water. (ASTM Designation D1193).

Procedure:
Transfer 80 mL of demineralized, deionized water into 2 clean 250 mL Erlenmeyer flasks. Transfer approximately 7 drops of Tashiro's indicator solution into each Erlenmeyer flask. Swirl the Erlenmeyer flasks to effect solution. Carefully adjust the color of the solutions in each Erlenmeyer flask to a neutral, straw color using either 0.02 N sodium hydroxide or 0.02 N hydrochloric acid. Note: if the solution is alkaline (>5.7 pH), the indicator will show a green color. This is adjusted with 0.02 N HCl to the neutral, straw color. If the solution is acidic (<5.7 pH), the indicator will show a red color. This is adjusted with 0.02 N NaOH to the neutral, straw color. Reserve one of the Erlenmeyer flasks as a reference color blank.

Transfer 20 g of molten caprolactam to the other Erlenmeyer flask. Swirl the Erlenmeyer flasks to effect solution. Note: if the caprolactam sample is solidified, place it in the hot water bath until completely molten. A syringe, capable of delivering 20 cc, is an acceptable transfer device, since the density of caprolactam is approximately 1.00 g/mL.

Compare the sample solution to the blank solution. If the sample solution is alkaline (green in color), using 0.02 N HCl, titrate carefully with swirling motions, until the solution reaches the neutral, straw color. If the sample solution is acidic (red in color), using 0.02 N NaOH, titrate carefully with swirling motions, until the solution reaches the neutral, straw color. If the sample solution remains the neutral, straw color, report the results as "neutral". Note: a calculated value of 0.00 is "neutral".

Calculations:

$$\text{Free Alkalinity (meq/Kg)} = (T \times N \times 1000)/W$$

Where:
T=titrant volume, mL
N=normality of 0.02 N HCl (meq/mL)
1000=Conversion factor, g to kg
W=sample weight, g $$\text{Free Acidity (meq/Kg)} = (T \times N \times 1000)/W$$

Where:
T=titrant volume, mL
N=normality of 0.02 N NaOH (meq/mL)
1000=Conversion factor, g to kg
W=sample weight, g For this procedure the density of caprolactam is assumed to be 1.00 g/mL; therefore 1 mL=1 g=1 cc. Report the results of free acidity and free alkalinity to the nearest 0.01 meq/kg. As determined by a single analyst, the standard deviation is 0.006 meq/kg at the 0.12 meq/kg level for 10 degrees of freedom.

QALAC-0007: Determination of Residue after Ignition of Pure Lactam or Caprolactam This analytical procedure describes the method for the determination of residue after ignition (ash) of finished product lactam and/or caprolactam. Standard hand and eye protection is required. Insulated gloves and sample tongs are required to use a muffle furnace. A fume hood is required when using a gas burner.

Special Tools/Equipment/Materials:
Platinum evaporating dish, 125 g (or equivalent)
Analytical balance, capable of weighing to +/−0.00001 g (preferred) or +/−0.0001 g
Gas burner
Muffle furnace
Metal desiccator (aluminum is preferred, but not required)
Glassware associated with standard analytical analysis
Glassware used is to be clean, unbroken, and of adequate size and volume capacity to perform this procedure. Adhering to these conditions, and dependent upon availability, technicians are empowered to select and use glassware for the completion of this procedure.
Materials:
Concentrated hydrochloric acid, reagent grade, as needed.
Purity of Reagents: reagent grade chemicals will be used in all tests. Unless otherwise indicated, it is intended that all reagents will conform to the specifications of the Committee on Analytical Reagents of the American Chemical Society, where such specifications are necessary.
Purity of Water: references to water shall be understood to mean reagent water conforming to the specifications for reagent water. (ASTM Designation ED 1193).

Procedure:

Heat a clean 125 g platinum evaporating dish in a muffle furnace set at approximately 800° C. for a minimum of 5 minutes. Note: it is standard practice to leave platinum evaporating dishes clean and inside the muffle furnace when not in use. If evaporating dishes are already in the muffle furnace, move to the next step.

Remove the evaporating dish from the muffle furnace and immediately place it into a metal desiccator. While monitoring the cooling time, allow the evaporating dish to cool to approximate room temperature. After cooling, weigh the evaporating dish and record the exact weight to the nearest 0.00001 g or 0.0001 g depending on the number of decimal places reported by the balance read out. Transfer approximately 100 g (record exact weight to the nearest 0.1 g) of sample into the evaporating dish. Place the evaporating dish containing the sample on a burner rack, under a well ventilated fume hood. Note: always handle the evaporating dish with tongs when filled with molten lactam or caprolactam. Heat the evaporating dish containing the sample over a low flame until the organic vapor ignites. After ignition of the vapor, remove the heat source.

After incineration, place the evaporating dish into a muffle furnace and heat at approximately 800° C. for a minimum of 15 minutes. Remove the evaporating dish from the muffle furnace and immediately place it into a metal desiccator. While monitoring the cooling time, allow the evaporating dish to cool to approximate room temperature. After cooling, weigh the evaporating dish and record the exact weight to the nearest 0.00001 g or 0.0001 g, depending on the number of decimal places reported by the balance read out. Thoroughly clean the evaporating dish and return it to the muffle furnace where it can remain until its next use.

Calculations:

$$\mu g/g \text{ (ppm) residue} = ((F-I) \times 10^6)/W$$

where:
F=final weight of evaporating dish (g)
I=initial weight of evaporating dish (g)
$10^6$=conversion factor to ppm
W=sample weight (g)

Report results to the nearest 1 μg/g (ppm) with values of less than 1 ppm being reported as <1 ppm. As determined by a single analyst, the standard deviation is 1.0 μg/g (ppm) at the 31 μg/g (ppm) level for 10 degrees of freedom.

QALAC-0009: Determination of Permanganate Number Seconds of Finished Product Lactam or Caprolactam This analytical procedure describes the method for the determination of the permanganate number seconds of finished product lactam and/or caprolactam. Standard hand and eye protection is required.

Special Tools/Equipment/Materials:
Glassware associated with standard analytical analysis
Dual beam Shimadzu UV-1601 spectrophotometer or equivalent
5 cm Pyrex cells
Time, with seconds capability
Matched 100 mL Nessler tubes (24 mm×375 mm) with 100 mL graduation mark and stoppers
Constant temperature bath, capable of maintaining 20° C.+/−0.5° C.
Glassware used is to be clean, unbroken, and of adequate size and volume capacity to perform this procedure. Adhering to these conditions, and dependent upon availability, technicians are empowered to select and use glassware for the completion of this procedure.
Materials:
Distilled water
0.01N potassium permanganate
PN seconds color reference standard Procedure:

Transfer approximately 50-80 mL of distilled water to a clean, dry 100 mL Nessler tube. Transfer 3.0 g (weighed to the nearest 0.01 g) of thoroughly mixed sample into the Nessler tube. Dilute to the 100 mL mark with distilled water. Obtain (or prepare) a second Nessler tube containing the color standard.

Transfer 1.0 mL of potassium permanganate to the Nessler tube containing the sample. Immediately after adding the potassium permanganate, start the timer or record the time to the nearest minute. Carefully invert the Nessler tube containing the sample to effect solution. Place both the Nessler tubes containing the blank solution and sample solution into the constant temperature bath. Monitor the color of the sample solution versus the color standard. As the color of the sample solution approaches the color of the standard solution, remove the Nessler tube from the constant temperature bath and read the absorbance on a spectrophotometer observing the following conditions:

Wavelength: 410 nm
Operating Mode: Absorbance
Reference: Distilled Water

Prior to the first sample analysis, empty the reference cell (if filled) and refill with fresh distilled water. Inspect the cell for cleanliness, clean as needed, and wipe dry. Insert the reference cell into the reference beam (rear position) in the cell compartment. Fill a clean 5 cm Pyrex cell (sample cell) with distilled water from the same source as the reference cell. Inspect the cell compartment windows for cleanliness and clean as needed. Place the sample cell in the sample beam (front position) of the cell compartment and close the compartment lid. Zero the spectrophotometer, observing the following conditions:

Wavelength: 410 nm
Operating Mode: Absorbance
Reference: Distilled Water

When the sample color matches the standard color, record the time in seconds. Verify that the visual color of the sample is in the absorbance range of 0.38 to 0.42. Record the actual elapsed time in seconds. This is the PN seconds value. Report the PN seconds value(s) to the nearest 1000.

QALAC-0011: Determination of Iron Content in Lactam or Caprolactam

This analytical procedure describes the method for the determination of Iron (Fe) content in caprolactam and/or lactam. Standard hand and eye protection is required. Due to the noxious fumes produced, a fume hood is required.

Special Tools/Equipment/Materials:
Glassware associated with standard analytical analysis
Analytical balance, capable of weighing to +/−0.01 g
Glass stirring rod
Hotplate
pH papers, pH scale 1-11, with pH/color chart
Shimadzu UV-1601, or equivalent double beam spectrophotometer
5 cm Pyrex cell
Cold bath (optional)
Platinum evaporating dish, 125 g (or equivalent)
Muffle Furnace
Metal desiccator (Aluminum preferred, but not required)
Glassware used is to be clean, unbroken, and of adequate size and volume capacity to perform this procedure. Adhering to these conditions, and dependent upon availability, technicians are empowered to select and use glassware for the completion of this procedure.

Materials:
Concentrated ammonium hydroxide, reagent grade
Concentrated hydrochloric acid, reagent grade
Concentrated glacial acetic acid, reagent grade
10% hydroxylamine hydrochloride solution
10% sodium acetate solution
0.2% 1,10-phenanthroline monohydrochloride monohydrate solution
Demineralized water
Purity of Reagents: reagent grade chemicals will be used in all tests. Unless otherwise indicated, it is intended that all reagents will conform to the specifications of the Committee on Analytical Reagents of the American Chemical Society, where such specifications are necessary.
Purity of Water: references to water shall be understood to mean reagent water conforming to the specifications for reagent water. (ASTM Designation ED 1193)

Procedure:
Transfer approximately 100 g (record exact weight to the nearest 0.1 g) of sample into a clean, dry 125 g capacity platinum evaporating dish. Place the evaporating dish containing the sample on a burner rack under a well ventilated fume hood. Heat the evaporating dish containing the sample over a low flame until the organic vapor ignites. After ignition of the vapor, remove the heat source. After incineration, place the evaporating dish into a muffle furnace and heat at approximately 800° C. for a minimum of 15 minutes. Remove the evaporating dish from the muffle furnace and immediately place it into a metal desiccator. After cooling to approximate room temperature, add 10 mL of concentrated hydrochloric acid to the evaporating dish.
Place the beaker onto a hotplate and bring the sample solution to a boil. Allow the solution to boil for a minimum of 5 minutes. Do not allow to boil dry. Add demineralized water as needed. Remove the evaporating dish from the heat source and cool.

Quantitatively transfer the solution into a 150 mL beaker using a small amount of demineralized water to rinse the inside of the evaporating dish into the beaker. Using a glass stirring rod, stir the solution while adding reagent grade concentrated ammonium hydroxide to adjust the pH level to 7+/−1. During this step, periodically touch the stirring rod to a dry strip of pH paper. Compare the color change of the pH paper to the pH color chart. Continue ammonium hydroxide addition until the proper pH range is obtained. Note: if the pH value exceeds 8, adjust it back to the proper pH range using reagent grade concentrated HCl.

After the proper pH range has been obtained, add 2 mL of reagent grade concentrated glacial acetic acid. Then add 5 mL of 10% hydroxylamine hydrochloride solution. Place the beaker onto a hotplate and bring the sample to a boil. Allow the solution to boil for a minimum of 5 minutes. Do not boil dry. Add demineralized water as needed.

Remove the beaker from the heat and rinse the walls with a small amount of demineralized water. Allow the solution to cool to approximate room temperature. Add 5 mL of 10% sodium acetate solution. Then add 10 mL of 0.2% 1,10-phenanthroline solution. Mix thoroughly. Transfer the solution quantitatively, using demineralized water, into a 100 mL volumetric flask. Dilute to the mark with demineralized water and mix thoroughly.

Prepare a reagent blank containing exact quantities of all reagents used and perform the operation in detail as outlined earlier. Using 5 cm Pyrex cells, zero the spectrophotometer observing the following conditions:

Wavelength: 510 nm
Operating Mode: Absorbance
Reference Cell: Demineralized Water
Sample Cell: Demineralized Water Determine the absorbance values of the blank and sample as follows:

Rinse the sample cell with blank/sample, refill, and shake to eliminate concentration lines. Then inspect the cell before reading the absorbance. Clean the outside of the cell and eliminate air bubbles as needed. Insert the cell into the cell compartment, close the compartment lid and allow the absorbance to stabilize before reading. Repeat the entire procedure for samples with an absorbance value greater than 0.700. Make the appropriate sample weight adjustment needed to effect an absorbance reading below 0.700. When analyzing multiple samples, rinse the sample cell between readings with the next sample to be read. When the analysis has been completed, thoroughly clean the cells and store them in the appropriate storage containers.

Calculations:

$$\mu g/g \ (ppm) \ Fe = [((S-B) \times F)] + b)/W$$

where:
S=sample absorbance
B=blank absorbance
F=instrument calibration factor (μg Fe/Abs unit)
W=sample weight (g)
b=instrument calibration factor (μg Fe)

Report results to the nearest 0.01 μg/g (ppm). Results of less than 0.01 μg/g (ppm) are to be reported as <0.01 μg/g (ppm). As determined by a single analyst, the standard deviation is 0.013 μg/g (ppm) at the 0.07 μg/g (ppm) level for 10 degrees of freedom.

QALAC-0012: Determination of the Volatile Base Content in Finished Product Lactam or Caprolactam This analytical procedure describes the method for the determination of the volatile base content of finished product lactam and/or caprolactam. A "neutral endpoint" is determined as the straw color between the green (alkaline) and the pink (acid) colors. Standard eye and hand protection is required.

Special Tools/Equipment/Materials:
Glassware associated with standard analytical analysis
Distillation apparatus comprising:
  Separatory/Addition Funnel (Kimax)
  Offset adapter, size 24/40 (as needed)
  "No hold up" condensers (Liebig)
  Kjeldahl trap adaptor
  Balloon flask with 2 or 3 vertical necks, 1000 mL capacity
  TEFLON® sleeves, size 24/40
  TYGON® tubing, sized to fit condensers, with appropriate clamps
Jack stand
Henegar granules
Cold water source for condensers
Heat source for distillation apparatus
5 or 10 mL microburette
Analytical balance, capable of weighing to +/−0.01 g
Glassware used is to be clean, unbroken, and of adequate size and volume capacity to perform this procedure. Adhering to these conditions, and dependent upon availability, technicians are empowered to select and use glassware for the completion of this procedure.
Materials:
0.02 N sodium hydroxide solution, standardized
0.02 N hydrochloric acid solution, standardized
4 N sodium hydroxide solution
distilled water
Tashiro's indicator solution
Purity of Reagents: reagent grade chemicals will be used in all tests. Unless otherwise indicated, it is intended that all reagents will conform to the specifications of the Committee on Analytical Reagents of the American Chemical Society, where such specifications are necessary.
Purity of Water: references to water shall be understood to mean reagent water conforming to the specifications for reagent water. (ASTM Designation ED 1193).
Procedure:
Prior to the first sample analysis clean the distillation apparatus as follows:

Carefully dismantle the apparatus. Thoroughly rinse the balloon flask, additional funnel, offset adaptor, Kjeldahl trap adaptor and stoppers with distilled water. Rinse the condenser tips and interior walls with distilled water, then reassemble the apparatus.

Add approximately 200 mL of distilled water and a few Hanegar Granules to the balloon flask and ensure that all joints are sealed. Note: Use TEFLON® sleeves where the joints meet. Do not use grease or silicon sealants. Position an empty beaker under the condenser tip and heat the balloon flask contents to boiling. Allow the balloon flask contents to boil for 15 to 20 minutes, then turn off the heat source and allow the apparatus to cool enough to be handled safely.

Check the normality of the 0.02 N sodium hydroxide solution daily. Using a microburette, transfer 10 mL of 0.02 N hydrochloric acid specifically designated for volatile base analysis to a 250 mL Erlenmeyer flask (or equivalent). Transfer approximately 8 drops of Tashiro's indicator solution to the same Erlenmeyer flask. Transfer approximately 50 mL of distilled water to the same Erlenmeyer flask. Using a microburette, titrate the solution with 0.02 N sodium hydroxide to a neutral endpoint. Record the volume of titrant used. Note: a neutral endpoint is determined as the straw color between the green (alkaline) and the pink (acid) colors.

Calculate the normality of the sodium hydroxide solution as follows:

$$\text{Normality} = (V \times N)/T$$

Where
  V=volume of 0.02N HCl, mL
  N=Normality of 0.02 N HCl
  T=Titrant volume of 0.02 N NaOH, mL Record the normality to the nearest 0.0001. If the normalities match, use the normality currently recorded on the solution label. If the normalities do not match, but are within 0.0002, replace the current normality on the label with the new normality. If the normalities do not match within 0.0002, the standardization must be performed in triplicate, observing all applicable conditions of standardization.

Prepare a blank solution containing exact quantities of all reagents to be used, but substitute 250 mL of distilled water for the dilute sample and perform the procedure as outlined earlier. Note: for this procedure, a blank solution must be prepared for each distillation apparatus to be used. The blank solution must be prepared before the sample solution is prepared.

Carefully dismantle the distillation apparatus and remove the beaker from below the delivery condenser. Thoroughly rinse the balloon flask, additional funnel, offset adaptor, Kjeldahl trap adaptor and stoppers with demineralized water. Rinse the condenser tips and interior walls with demineralized water.

Using a microburette, transfer 10.00 mL of 0.02 N HCl solution into a 250 mL Erlenmeyer flask. Transfer 30 mL of distilled water to the same flask. Transfer approximately 8 drops of Tashiro's indicator solution to the same flask. Position the 250 mL Erlenmeyer flask on a jack stand, under the tip of the condenser delivery tube, so the delivery tube tip is below the liquid surface. Transfer approximately 50 g (record the exact weight to the nearest 0.01 g) of sample and 230 mL of distilled water to the balloon flask. Transfer 6-10 Henegar Granules to the same balloon flask. Reassemble the distillation apparatus. Upon completion of the assembly of the apparatus, transfer 50 mL of 4 N sodium hydroxide to the addition funnel. Opening the addition funnel stopcock, transfer the above-mentioned 4 N NaOH to the balloon flask, closing the stopcock as soon as the transfer is complete. Heat the balloon flask to boiling and distill the solution until approximately 100 mL of distillate is collected in the 250 mL flask.

After collection of approximately 100 mL of distillate lower the jack stand under the 250 mL flask until the delivery tube tip is above the surface of the liquid. Turn off the heat source. The delivery tube must be above the liquid level or the solution will siphon up the delivery tube and back into the balloon flask. Rinse the tip of the delivery tube into the 250 mL flask with a small amount of distilled water. Using a 10 mL microburette, titrate the solution with 0.02 N sodium hydroxide solution to the neutral endpoint described earlier. Record the volume of titrant used.

Calculations:

$$\text{Volatile Bases as NH}_3 \text{ (ppm)} = ((B-S) \times N \times F \times 10^3)/W$$

Where
  B=volume of titrant, mL (blank)
  S=volume of titrant, mL (sample)

N=normality of 0.02 N NaOH, meq/mL
F=17.03 mg $NH_3$/meq
$10^3$=conversion factor, μg/mg (ppm)
W=sample weight, g Report results to the nearest 0.1 μg/g (ppm). Results of less than 0.1 μg/g (ppm) are to be reported as <0.1 μg/g (ppm). As determined by a single analyst, the standard deviation is 0.40 μg/g (ppm) at the 4.9 μg/g (ppm) volatile bases level for 10 degrees of freedom.

QALAC-0033: Determination of Percent Transmission (% T) of Finished Product Lactam or Caprolactam This analytical procedure describes the method for the determination of percent transmission (% T) of finished product lactam and/or caprolactam. Standard hand and eye protection are required.

Special Tools/Equipment/Materials:
Glassware associated with standard analytical analysis
Dual beam spectrophotometer, Shimadzu UV-1601 or equivalent
1 cm silica cells
Analytical balance3, capable of weighing to 0.01 g
Hot water bath
100 mL volumetric flask or equivalent
150 mL beaker or equivalent
Cool water bath
Drying oven
Glassware used is to be clean, unbroken, and of adequate size and volume capacity to perform this procedure. Adhering to these conditions, and dependent upon availability, technicians are empowered to select and use glassware for the completion of this procedure.

Materials:
Distilled Water
Purity of Water: references to water shall be understood to mean reagent water conforming to the specifications for reagent water. (ASTM Designation ED 1193).

Procedure:
Transfer about 25 g of distilled water to a 150 mL beaker. Transfer 50+/−0.50 g of finished product lactam and/or caprolactam into the 150 mL beaker. Solidified caprolactam must be molten and thoroughly mixed prior to analysis. Loosen the cap on the sample bottle and place the sample in a drying oven set at 80-150° C. until the caprolactam is partially molten. Remove the caprolactam sample from the oven and immerse the bottle in a hot water bath until the caprolactam is completely molten. Carefully tighten the lid on the sample bottle and invert several times to mix the caprolactam. Note: caprolactam should be weighed as soon as possible after becoming fully molten, since overheating may affect the analysis. Flake caprolactam does not need to be melted prior to sample analysis.

Using a glass stirring rod, gently agitate the sample/water mixture until mixed thoroughly. Transfer the sample/water mixture into a 100 mL volumetric flask, rinsing the beaker into the volumetric with distilled water. Cap the volumetric flask. Allow the volumetric flask to cool to approximately room temperature. Dilute with distilled water. Invert and shake the sample to thoroughly mix the solution. Note: a cool water bath may be used to aid cooling.

Prior to the first sample analysis, inspect the 1 cm silica cells and, if necessary, clean each one with cell cleaning solution. Rinse the cells with distilled water.

Fill the clean silica cells with distilled water. Inspect the cell compartment windows for cleanliness and clean as needed. Place the sample cell in the sample beam (front position) and the reference cell in the reference beam (rear position) of the cell compartment and close the compartment cover.

Zero the spectrophotometer, observing the following conditions:
Wavelength=290 nm
Operating Mode=% Transmission
Reference=Distilled Water Rinse the sample cell with the sample solution. Refill the cell with sample. Cap the cell and invert as necessary to eliminate concentration gradient lines and/or air bubbles in the cell. Inspect the cell for cleanliness, concentration lines and air bubbles before proceeding. Insert the cell into the sample beam (front position in the cell compartment), close the compartment cover, and allow the digital readout to stabilize before printing or recording the result. The percent transmission is read directly from the instrument readout. Print or record the reading.

When analyzing multiple samples, rinse the cell between readings using the next sample to be analyzed. When all analyses are complete, thoroughly rinse the sample cell with warm water followed by distilled water. Refill the sample cell with distilled water. Report the % Transmission to the nearest 0.1%.

Conventional Caprolactam Production

A conventional crude caprolactam production method contains the following operations starting with cyclohexanone oxime:
a. Rearrangement
b. Toluization/Neutralization/Separation (TNS Step)

During the Rearrangement step(s), cyclohexanone oxime (oxime) undergoes a Beckmann rearrangement to form caprolactam. The rearrangement reaction can be catalyzed by sulfuric acid, sulfur trioxide or oleum, which is synonymous with fuming sulfuric acid. Oxime (ketoxime) and oleum (catalyst) are fed to the rearrangers which are recirculating plug flow reactors (loop reactors). The resulting mixture of caprolactam (amide) and sulfuric acid, in this example, is referred to as the rearrangement mass. Impurities are produced as a byproduct of the rearrangement reaction of oxime to caprolactam. These impurities include pyrazine precursors and sulfonated organic compounds. The rearrangement mass is then sent to the Toluization/Neutralization/Separation phase.

In the Toluization/Neutralization/Separation (TNS) phase, the rearrangement mass is mixed with water, ammonia (base) and toluene (solvent) in a recirculating plug flow reactor (loop reactor). Aqueous ammonium sulfate is produced, and caprolactam is extracted into an organic caprolactam/toluene phase. The caprolactam/toluene mixture is phase separated from the aqueous sulfate. The toluene/caprolactam mixture is then separated through vacuum distillation of the toluene. The toluene is recycled and the crude caprolactam is sent to the purification phase. Caprolactam in the aqueous ammonium sulfate phase is removed by extraction with toluene. Residual toluene is removed from the aqueous ammonium sulfate by phase separation followed by vacuum distillation. The toluene is recycled and the aqueous ammonium sulfate is sent for further processing to fertilizer or otherwise recycled or disposed of according to commonly accepted industry practices and standards.

Conventional Caprolactam Purification

A conventional crude caprolactam purification method contains the following steps:
  a. Crude Caprolactam Concentration and Filtration
  b. Caprolactam Crystallization
  c. Monomer Drying and Loading In the Crude Caprolactam Concentration and Filtration operation, the water content of the crude caprolactam is reduced by vacuum distillation. The pH of the caprolactam stream is then adjusted by caustic addition, and any precipitated sodium sulfate crystals are removed by filtration.

During Caprolactam Crystallization, a two stage vacuum cooled crystallization process removes impurities from the crude caprolactam. Caprolactam crystals are separated from mother liquor. The mother liquor contains the concentrated impurities. A mother liquor purge is then taken from the first stage of each crystallization train and sent to be recycled with the caprolactam recovered, and the impurities rejected as a solid waste.

During Monomer Drying and Loading, water is removed from the purified caprolactam prior to storage and product loading. Drying is achieved through flashing water under vacuum conditions. The dry purified caprolactam is then either sent to a central shipping point, so that it can be shipped to other locations, or is sent to a flaking operation for additional processing into flakes.

Product specifications for the molten caprolactam—conventional-grade are shown below:

| PARAMETERS | VALUE | TEST METHOD |
|---|---|---|
| Color, APHA | 5 max. | QALAC-0001 |
| Permanganate Index (ISO) | 9 max. | QALAC-0002 |
| Water, % | 0.20 max. | QALAC-0005 |
| Iron (as Fe), ppm | 0.5 max | QALAC-0011 |
| Volatile Base (as NH3), ppm | 10 max | QALAC-0012 |
| Volatile Base (as NH3), meq/kg | 0.59 max | QALAC-0012 |
| Free Alkalinity, meq/kg | 0.08 max | QALAC-0006 |
| Free Acidity, meq/kg | 0.05 max | QALAC-0006 |
| Ash, ppm | 55 max | QALAC-0007 |

Caprolactam Production—A

An improved crude caprolactam production consists of the following operations starting with oxime:
  a. Rearrangement
  b. Rearrangement Mass Heat Treatment
  c. Toluization/Neutralization/Separation (TNS Step)

During the Rearrangement step(s), cyclohexanone oxime (oxime) undergoes a Beckmann rearrangement to form caprolactam. The rearrangement reaction is catalyzed by oleum, which is synonymous with fuming sulfuric acid. Oxime (ketoxime) and oleum (catalyst) are fed to the rearrangers. The resulting mixture of caprolactam (amide) and sulfuric acid, in this example, is referred to as the rearrangement mass. Impurities are produced as a byproduct of the rearrangement reaction of oxime to caprolactam. These impurities include pyrazine precursors and sulfonated organic compounds. The rearrangement mass is then sent to the Rearrangement Mass Heat Treatment stage.

During the Rearrangement Mass Heat Treatment stage, the rearrangement mass from the Rearrangement stage is heated to between about 120° C. and about 125° C. and held at that temperature for about 4 to about 16 minutes. The heat treatment step substantially removes one major caprolactam impurity in the final product: 2-hydroxycyclohexanone-sulfonic acid (2HCOSA). The heat treatment step also sulfonates the precursor to the caprolactam impurity OHP. The sulfonated precursor leads to sulfonated octahydrophenazine (SOHP) in the impure caprolactam. SOHP is fairly easy to remove from the impure caprolactam by distillation.

In the Toluization/Neutralization/Separation (TNS) phase, the rearrangement mass is mixed with water, ammonia (base) and toluene (solvent) in a recirculating plug flow reactor. Aqueous ammonium sulfate is produced, and caprolactam is extracted into an organic caprolactam/toluene phase. The caprolactam/toluene mixture is phase separated from the aqueous sulfate. The toluene/caprolactam mixture is then separated through vacuum distillation of the toluene. The toluene is recycled and the crude caprolactam is sent to the purification phase.

Caprolactam Production—B

Another improved crude caprolactam production consists of the following operations:
  a. Rearrangement
  b. Rearrangement Mass Heat Treatment
  c. Toluization/Neutralization/Separation (TNS Step)

During the Rearrangement step(s), cyclohexanoneoxime (oxime) undergoes a Beckmann rearrangement to form caprolactam. The rearrangement reaction is catalyzed by oleum, which is synonymous for fuming sulfuric acid. Oxime (ketoxime) and oleum (catalyst) are fed to the rearrangers. The resulting mixture of caprolactam (amide) and sulfuric acid, in this example, is referred to as the rearrangement mass. Impurities are produced as a byproduct of the rearrangement reaction of oxime to caprolactam. These impurities include pyrazine precursors and sulfonated organic compounds. The rearrangement mass is then sent to the Rearrangement Mass Heat Treatment stage.

During the Rearrangement Mass Heat Treatment stage, the rearrangement mass from the Rearrangement stage is heated to between about 125° C. and about 130° C. and held at that temperature for about 1 to about 4 minutes. The heat treatment step substantially removes one major caprolactam impurity in the final product: 2-hydroxycyclohexanone-sulfonic acid (2HCOSA). The heat treatment step also sulfonates the precursor to the caprolactam impurity OHP. The sulfonated precursor leads to sulfonated octahydrophenazine (SOHP) in the impure caprolactam. SOHP is fairly easy to remove from the impure caprolactam by distillation.

In the Toluization/Neutralization/Separation (TNS) phase, the rearrangement mass is mixed with water, ammonia (base) and toluene (solvent) in a recirculating plug flow reactor. Aqueous ammonium sulfate is produced, and caprolactam is extracted into an organic caprolactam/toluene phase. The caprolactam/toluene mixture is phase separated from the aqueous sulfate. The toluene/caprolactam mixture is then separated through vacuum distillation. The toluene is recycled and the crude caprolactam is sent to the purification phase.

Caprolactam Production—C

Another improved crude caprolactam production consists of the following operations:
  a. Rearrangement
  b. Rearrangement Mass Heat Treatment
  c. Toluization/Neutralization/Separation (TNS Step)

During the Rearrangement step(s), cyclohexanoneoxime (oxime) undergoes a Beckmann rearrangement to form caprolactam. The rearrangement reaction is catalyzed by oleum, which is synonymous for fuming sulfuric acid. Oxime (ketoxime) and oleum (catalyst) are fed to the rearrangers. The resulting mixture of caprolactam (amide) and sulfuric acid, in this example, is referred to as the rearrangement mass. Impurities are produced as a byproduct of the rearrangement reaction of oxime to caprolactam. These impurities include pyrazine precursors and sulfonated organic compounds. The rearrangement mass is then sent to the Rearrangement Mass Heat Treatment stage.

During the Rearrangement Mass Heat Treatment stage, the rearrangement mass from the Rearrangement stage is heated to between about 115° C. and about 130° C. and held at that temperature for about 1 to about 30 minutes. The heat treatment step substantially removes one major caprolactam impurity in the final product: 2-hydroxycyclohexanone-sulfonic acid (2HCOSA). The heat treatment step also sulfonates the precursor to the caprolactam impurity OHP. The sulfonated precursor leads to sulfonated octahydrophenazine (SOHP) in the impure caprolactam. SOHP is fairly easy to remove from the impure caprolactam by distillation.

In the Toluization/Neutralization/Separation (TNS) phase, the rearrangement mass is mixed with water, ammonia (base) and toluene (solvent) in a recirculating plug flow reactor. Aqueous ammonium sulfate is produced, and caprolactam is extracted into an organic caprolactam/toluene phase. The caprolactam/toluene mixture is phase separated from the aqueous sulfate. The toluene/caprolactam mixture is then separated through vacuum distillation. The toluene is recycled and the crude caprolactam is sent to the purification phase.

Caprolactam Purification

The crude caprolactam from an improved production process is then sent to an improved purification process. There are 3 primary operations of the improved purification process:

a. Crude Caprolactam Concentration and Filtration
b. Caprolactam Crystallization
c. Monomer Distillation, Drying and Loading (improved caprolactam)

In the Crude Caprolactam Concentration and Filtration operation, the water content of the crude caprolactam is reduced by vacuum distillation. The pH of the caprolactam stream is then adjusted by caustic addition, and any precipitated sodium sulfate crystals are removed by filtration.

During Caprolactam Crystallization, a two stage vacuum cooled crystallization process removes impurities from the crude caprolactam. Caprolactam crystals are separated from mother liquor. The mother liquor contains the concentrated impurities. The crystals are remelted, and sent forward to Monomer Distillation, Drying, and Loading.

Monomer Distillation, Drying and Loading incorporates single stage vacuum flashers to partially dewater the caprolactam. The final water removal, along with the removal of heavy impurities is achieved with a vacuum distillation column. The resulting improved caprolactam is then sent to a central shipping point, so that it can be shipped as a molten product, or is sent to a flaking operation.

The product specification for the caprolactam from the improved processes is shown below:

| PARAMETERS | VALUE | TEST METHOD |
| --- | --- | --- |
| Color, APHA | 5 max. | QALAC-0001 |
| Permanganate Index (ISO) | 5 max. | QALAC-0002 |
| Permanganate Number Seconds | 15,000 min. | QALAC-0009 |
| Water, % | 0.10 max. | QALAC-0005 |
| Iron (as Fe), ppm | 0.5 max | QALAC-0011 |
| Volatile Base (as NH3), ppm | 10 max | QALAC-0012 |
| Volatile Base (as NH3), meq/kg | 0.59 max | QALAC-0012 |
| Free Alkalinity, meq/kg | 0.05 max | QALAC-0006 |
| Free Acidity, meq/kg | 0.05 max | QALAC-0006 |
| Ash, ppm | 10 max | QALAC-0007 |
| Transmittance @ 290 nm, % | ≧90 min | QALAC-0033 |

Thus, specific embodiments and applications of the production and purification of amides, methods and uses thereof have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

We claim:

1. An impure amide product comprising an amide-based composition, wherein the amide-based composition comprises a heated rearrangement mass, wherein the heated rearrangement mass comprises at least one amide, at least one catalyst and at least one impurity that has been broken down, sulfonated or otherwise significantly reduced in concentration, and wherein the rearrangement mass has been prepared by heating to a temperature of at least about 115° C. for a period of time in order to sulfonate some of the at least one impurity in the rearrangement mass; and
water, at least one base and at least one solvent.

2. The impure amide product of claim 1, wherein the amide-based composition comprises a dual-phase liquid.

3. The impure amide product of claim 2, wherein the dual-phase liquid comprises an aqueous phase and an organic phase.

4. The impure amide product of claim 3, wherein the aqueous phase comprises the water and an acid salt formed from the at least one base.

5. The impure amide product of claim 3, wherein the organic phase comprises the at least one solvent and the at least one amide.

* * * * *